United States Patent [19]

Andree et al.

[11] Patent Number: 4,952,235

[45] Date of Patent: Aug. 28, 1990

[54] (HETERO)ARYLOXYNAPHTHALENES HAVING SUBSTITUENTS BONDED VIA SULPHUR

[75] Inventors: Roland Andree, Langenfeld; Michael Haug, Bergisch-Gladbach; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 370,354

[22] Filed: Jun. 22, 1989

[30] Foreign Application Priority Data

Jul. 9, 1988 [DE] Fed. Rep. of Germany ....... 3823318

[51] Int. Cl.$^5$ .................. A01N 43/40; C07C 323/17; C07C 255/50; C07C 317/12; C07C 211/72
[52] U.S. Cl. ......................... 71/94; 71/98; 71/103; 546/288; 546/293; 546/294; 546/295; 546/300; 558/413; 558/414; 558/418; 558/419; 558/422; 558/424; 560/10; 568/27; 568/28; 568/30; 568/33; 568/39; 568/44; 568/49
[58] Field of Search .................. 568/27, 28, 30, 33, 568/39, 44, 49; 571/84, 98, 103; 546/288, 293, 294, 295, 300; 560/10; 558/413, 414, 418, 419, 422, 424

[56] References Cited

U.S. PATENT DOCUMENTS 4,233,054  11/1980  Szczeponski et al. .................. 71/109
4,521,426   6/1985  Cain ..................................... 514/346
4,709,077  11/1987  Harre et al. ........................... 71/109

FOREIGN PATENT DOCUMENTS 2223894  5/1972  Fed. Rep. of Germany.
2520815  11/1976  Fed. Rep. of Germany.
2366040   7/1977  Fed. Rep. of Germany.

Primary Examiner—Werren B. Lone
Assistant Examiner—Vera C. Clarke
Attorney, Agent, or Firm—Sprung, Horn, Kramer & Woods

[57] ABSTRACT (Hetero) aryloxynaphthalenes having substituents bonded via sulphur having herbicidal activity and of the formula

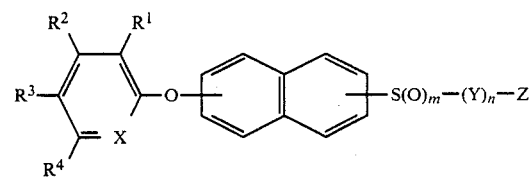

in which
m represents the number 0, 1 or 2,
n represents the numbers 0 or 1,
$R^1$ represents hydrogen, halogen, cyano or trifluoromethyl,
$R^2$ represents hydrogen or halogen,
$R^3$ represents halogen, trifluoromethyl, trifluoromethoxy, trifluoromethylthio or trifluoromethylsulphonyl,
$R^4$ represents hydrogen or halogen,
X represents nitrogen or the group C—$R^5$, wherein
$R^5$ represents hydrogen or halogen,
Y represents oxygen or one of the groupings

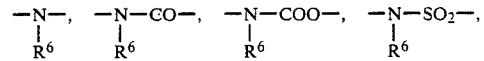

wherein
$R^6$ represents hydrogen, alkyl, —CO—Z or —SO$_2$—Z and
Z represents hydrogen, halogen or an optionally substituted alkyl, cycloalkyl, cycloalkylalkyl, alkenyl, alkinyl, aryl or heteroaryl radical.

7 Claims, No Drawings

(HETERO)ARYLOXYNAPHTHALENES HAVING SUBSTITUENTS BONDED VIA SULPHUR

The invention relates to new (hetero)aryloxynaphthalenes having substituents bonded via sulphur, processes and new intermediate products for their preparation and their use as herbicides.

It is already known that certain dioxy-benzene derivatives, such as, for example, methyl α-[4-(2,4-dichlorophenoxy)-phenoxy]-propionate (diclofop-methyl), have a herbicidal action (compare DE-OS (German Published Specification) No. 2,223,894). However, the action of these known compounds against weeds and their crop plant tolerability are not always satisfactory. New (hetero)aryloxynaphthalenes having substituents bonded via sulphur and of the general formula (I)

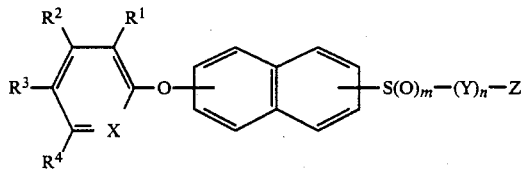

in which
  m represents the numbers 0, 1 or 2,
  n represents the numbers 0 or 1,
  $R^1$ represents hydrogen, halogen, cyano or trifluoromethyl,
  $R^2$ represents hydrogen or halogen,
  $R^3$ represents halogen, trifluoromethyl, trifluoromethoxy, trifluoromethylthio or trifluoromethylsulphonyl,
  $R^4$ represents hydrogen or halogen,
  X represents nitrogen or the grouping C-$R^5$, wherein
  $R^5$ represents hydrogen or halogen,
  Y represents oxygen or one of the groupings

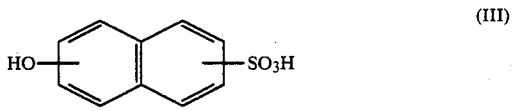

wherein
  $R^6$ represents hydrogen, alkyl, —CO—Z or —$SO_2$—Z and
  Z represents hydrogen, halogen or an optionally substituted radical from the series comprising alkyl, cycloalkyl, cycloalkylalkyl, alkenyl, alkinyl, aralkyl, aryl and heteroaryl,
and salts of compounds of the formula (I) (for example where Z=metal equivalent) have now been found.

It has furthermore been found that the new (hetero)aryloxynaphthalenes having substituents bonded via sulphur and of the general formula (I) are obtained by a process in which (a) in the case where m represents 2, n represents 1, Y represents oxygen, Z represents hydrogen or a metal equivalent and $R^1$, $R^2$, $R^3$, $R^4$ and X have the above-mentioned meanings, halogeno-(hetero)aryl compounds of the general formula (II)

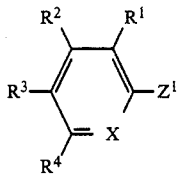

in which
  $R^1$, $R^2$, $R^3$, $R^4$ and X have the above-mentioned meanings and
  $Z^1$ represents halogen,
are reacted with hydroxynaphthalenesulphonic acids of the general formula (III)

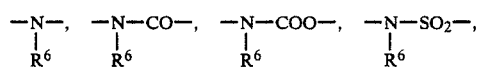

or metal salts thereof
if appropriate in the presence of an acid acceptor and if appropriate in the presence of a diluent, and, if appropriate, the products are then treated with a strong acid, or by a process in which (b) in the case where m represents the numbers 0, 1 or 2, n represents the number 0, Z represents halogen and $R^1$, $R^2$, $R^3$, $R^4$ and X have the above-mentioned meanings,
compounds of the general formula (I) in which m represents the numbers 0, 1 or 2, n represents the number 1, Y represents oxygen, Z represents hydrogen or a metal equivalent and $R^1$, $R^2$, $R^3$, $R^4$ and X have the above-mentioned meanings,
are reacted with a halogenating agent, if appropriate in the presence of a catalyst or halogenating auxiliary and if appropriate in the presence of a diluent, or by a process in which (c) in the case where m represents the numbers 0, 1 or 2, n represents the number 0, Z represents hydrogen or a metal equivalent and $R^1$, $R^2$, $R^3$, $R^4$ and X have the above-mentioned meanings,
compounds of the general formula (I) in which m represents the number 2, n represents the number 0, Z represents halogen and $R^1$, $R^2$, $R^3$, $R^4$ and X have the above-mentioned meanings,
are reacted with a reducing agent, if appropriate in the presence of a reduction auxiliary and if appropriate in the presence of a diluent, or by a process in which (d) in the case where m represents the numbers 0, 1 or 2, n represents the number 1 and $R^1$, $R^2$, $R^3$, $R^4$, X, Y and Z have the above-mentioned meanings,
compounds of the formula (I) in which m represents the numbers 0, 1 or 2, n represents the number 0, Z represents halogen and $R^1$, $R^2$, $R^3$, $R^4$ and X have the above-mentioned meanings,
are reacted with nucleophilic compounds of the general formula (IV)

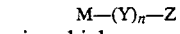  M—(Y)$_n$—Z  (IV)

in which
  n, Y and Z have the above-mentioned meanings and
  M represents hydrogen or a metal equivalent,
if appropriate in the presence of an acid acceptor and if appropriate in the presence of a diluent, or by a process in which (e) in the case where Z has the above-mentioned meaning, with the exception of hydrogen and halogen, and m, n, $R^1$, $R^2$, $R^3$, $R^4$, X and Y have the above-mentioned meanings, compounds of the formula (I) in which Y represents oxygen or NH, Z represents hydrogen and m, n, $R^1$, $R^2$, $R^3$, $R^4$ and X have the abovementioned meanings, are reacted with electrophilic compounds of the general formula (V)

$$Z^2-(Y^1)n-Z^3 \qquad (V)$$

in which
  n represents the numbers 0 or 1,
  $Y^1$ represents CO or $SO_2$,
  $Z^2$ represents halogen and
  $Z^3$ has the meaning given above for Z, with the exception of hydrogen and halogen, and if appropriate in the presence of an acid acceptor and if appropriate in the presence of a diluent, and, if appropriate, salts are prepared by customary methods from the compounds of the formula (I) prepared by the processes described above.

Finally, it has been found that the new (hetero)aryloxynaphthalenes having substituents bonded via sulphur and of the formula (I) have outstanding herbicidal properties.

Surprisingly, the (hetero)aryloxynaphthalenes having substituents bonded via sulphur and of the formula (I) have a considerably more potent action against weeds than methyl α-[4-(2,4-dichloro-phenoxy)-phenoxy]-propionate, which is a structurally similar already known active compound of the same type of action.

The invention preferably relates to compounds of the formula (I) in which
  m represents the numbers 0, 1 or 2,
  n represents the numbers 0 or 1,
  $R^1$ represents hydrogen, fluorine, chlorine, bromine, cyano or trifluoromethyl,
  $R^2$ represents hydrogen, fluorine or chlorine,
  $R^3$ represents fluorine, chlorine, bromine, trifluoromethyl, trifluoromethoxy, trifluoromethylthio or trifluoromethylsulphonyl,
  $R^4$ represents hydrogen, fluorine or chlorine,
  X represents nitrogen or the grouping C-$R^5$, wherein
  $R^5$ represents hydrogen, fluorine, chlorine or bromine,
  Y represents oxygen or one of the groupings

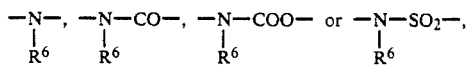

wherein
  $R^6$ represents hydrogen, $C_1$-$C_4$-alkyl, —CO—Z or —$SO_2$—Z and
  Z represents hydrogen or halogen, or $C_1$-$C_6$-alkyl which is optionally substituted by halogen, cyano, carboxyl, $C_1$-$C_4$-alkoxy, $C_1$-$C_4$-alkylcarbonyl, $C_1$-$C_4$-alkoxy-carbonyl $C_1$-$C_4$-alkoxy-carbonyl-$C_1$-$C_4$-alkoxy- and/or $C_1$-$C_4$-alkylamino-carbonyl, or $C_3$-$C_6$-cycloalkyl or $C_3$-$C_6$-cycloalkyl-$C_1$-$C_4$-alkyl, in each case optionally substituted by halogen and/or $C_1$-$C_4$-alkyl; or $C_2$-$C_6$-alkenyl or $C_2$-$C_6$-alkinyl, in each case optionally substituted by halogen, cyano, carboxyl and/or $C^1$-$C_4$-alkoxy-carbonyl; or phenyl, naphthyl, phenyl-Cl-$C_4$-alkyl or naphthyl-$C_1$-$C_4$-alkyl, in each case optionally substituted by halogen, cyano, carboxyl, nitro, $C_1$-$C_4$-alkyl, $C_1$-$C_2$-halogenoalkyl, $C_1$-$C_4$-alkoxy, $C_1$-$C_2$-halogenoalkoxy, $C_1$-$C_4$-alkylthio, $C_1$-$C_2$-halogenoalkylthio, $C_1$-$C_4$-alkylsulphinyl, $C_1$-$C_4$-alkylsulphonyl, di-($C_1$-$C_2$-alkyl)-aminosulphonyl, di-($C_1$-$C_2$-alkyl)-aminocarbonyl, di-($C_1$-$C_2$-alkyl)-amino, $C_1$-$C_4$-alkoxy-carbonyl and/or $C_1$-$C_2$-alkylenedioxy, or represents a heterocyclic radical from the series comprising pyrazolyl, imidazolyl and triazolyl, which is optionally substituted by halogen, $C_1$-$C_4$-alkyl, $C_1$-$C_2$-halogeno-alkyl, $C_1$-$C_4$-alkoxy and/or $C_1$-$C_2$-halogenoalkoxy.

The invention particularly relates to compounds of the formula (I) in which
  $R^1$ represents cyano, fluorine or chlorine,
  $R^2$ represents hydrogen, fluorine or chlorine,
  $R^3$ represents chlorine, trifluoromethyl or trifluoromethylsulphonyl,
  $R^4$ represents hydrogen, fluorine or chlorine,
  X represents nitrogen or the grouping C—$R^5$, wherein
  $R^5$ represents hydrogen, fluorine or chlorine, and
  (A) m represents the number 0,
  n represents the number 0,
  Z represents hydrogen, $C_1$-$C_4$-alkyl which is optionally substituted by fluorine, chlorine, cyano, carboxyl, $C_1$-$C_4$-alkoxycarbonyl, $C_1$-$C_4$-alkoxy-carbonyl-$C_1$-$C_2$-alkoxy-carbonyl and/or $C_1$-$C_4$-alkylamino-carbonyl, or $C_3$-$C_4$-alkenyl which is optionally substituted by fluorine, chlorine, cyano, carboxyl and/or $C_1$-$C_4$-alkoxycarbonyl or benzyl which is optionally substituted by fluorine, chlorine and/or methyl, or
  (B) m represents the number 2,
  n represents the numbers 0 or 1,
  Y represents oxygen or one of the groupings —NH—, —NH—CO—, —NH—COO— or —NH—$SO_2$—, and
  Z represents hydrogen, or $C_1$-$C_4$-alkyl which is optionally substituted by fluorine, chlorine, cyano, carboxyl, $C_1$-$C_4$-alkoxy-carbonyl and/or $C_1$-$C_4$-alkylamino-carbonyl; or $C_3$-$C_4$-alkenyl which is optionally substituted by fluorine chlorine, cyano, carboxyl and/or $C_1$-$C_4$-alkoxycarbonyl; or phenyl or benzyl, in each case optionally substituted by fluorine, chlorine, bromine, nitro, methyl, ethyl, trifluoromethyl, methoxy, ethoxy, difluoromethoxy, trifluoromethoxy, chlorodifluoromethoxy, methylthio, difluoromethylthio, trifluoromethylthio, chlorodifluoromethylthio, methylsulphonyl, dimethylaminosulphonyl, methoxycarbonyl and/or ethoxy-carbonyl, or
  (C) m represents the number 2,
  n represents the number 0 and
  Z represents chlorine, pyrazolyl which is optionally substituted by chlorine and/or $C_1$-$C_3$-alkyl, or imidazolyl which is optionally substituted by $C_1$-$C_3$-alkyl.

Especially preferred groups of compounds of the formula (I) are those of the following formulae

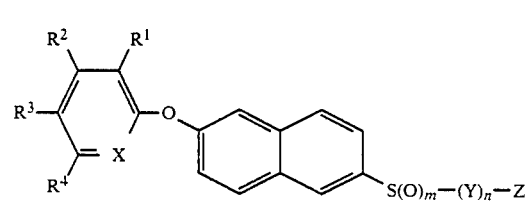

(Ia)

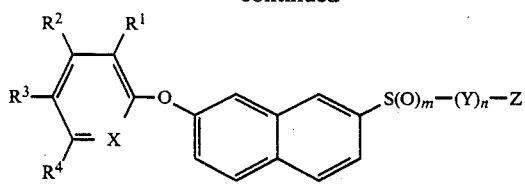

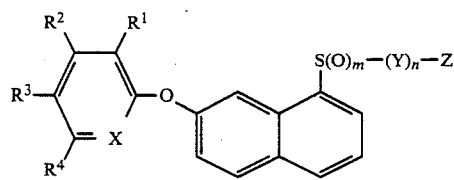

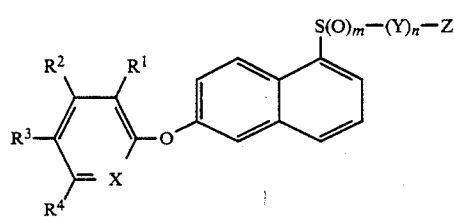

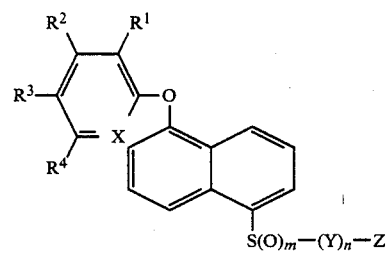

in which in each case m, n, R$^1$, R$^2$, R$^3$, R$^4$, X, Y and Z have the meanings mentioned above as particularly preferred.

The invention furthermore preferably relates to salts of compounds of the formula (I) in which R$^1$, R$^2$, R$^3$, R$^4$, X, Y, Z, m and n have the above-mentioned meanings, where these contain —COOH, —SO$_3$H, —CO—NH— or —SO$_2$—NH— groups, and bases, such as, preferably, the hydroxide, hydride, amide or carbonate of sodium, potassium or calcium, the C$_1$–C$_4$-alkanolates of sodium or potassium, ammonia, C$_1$–C$_4$-alkylamines, di-(C$_1$–C$_4$-alkyl)-amines or tri-(C$_1$–C$_4$-alkyl)-amines.

If 3,4-dichloro-benzotrifluoride and potassium 7-hydroxy-naphthalene-2-sulphonate are used as starting substances for process (a) according to the invention, the course of the reaction can be represented by the following equation:

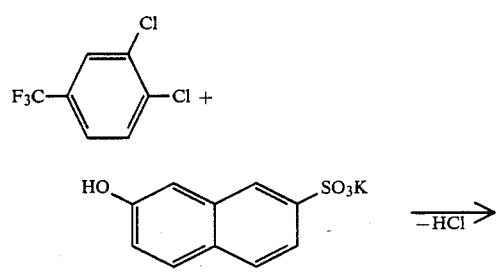

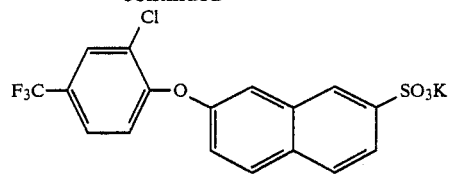

If 6-(2-chloro-6-fluoro-4-trifluoromethyl-phenoxy)-naphthalene-2-sulphonic acid and phosphorus(V) chloride are used as starting substances for process (b) according to the invention, the course of the reaction can be represented by the following equation:

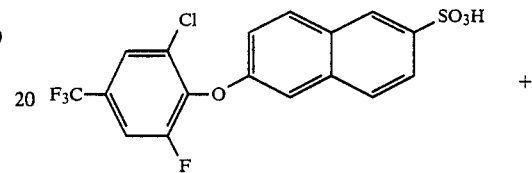

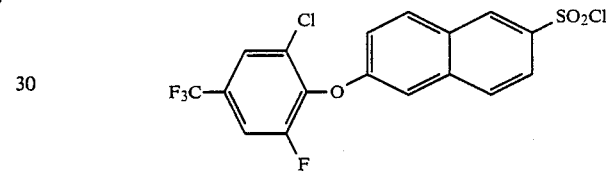

If 5-(2-fluoro-4-trifluoromethyl-phenoxy)-naphthalene-1-sulphonyl chloride and sodium sulphite are used as starting substances for process (c) according to the invention, the course of the reaction can be represented by the following equation:

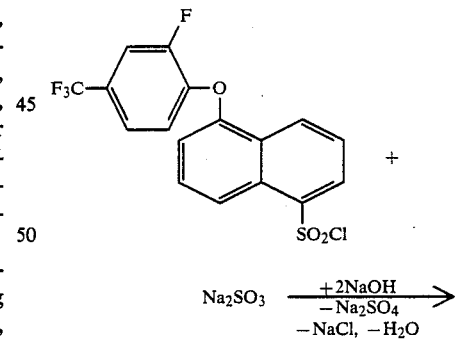

If 6-(3,5-dichloro-pyridin-2-yl-oxy)-naphthalene-1-sulphonyl chloride and ethyl aminoacetate are used as starting substances for process (d) according to the invention, the course of the reaction can be represented by the following equation;

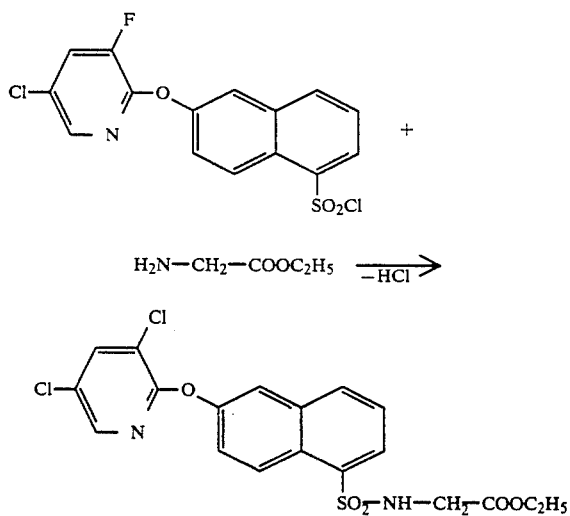

If 7-(3-chloro-5-trifluoromethyl-pyridin-2-yl-oxy)-naphthalen-1-yl-mercaptan and ethyl chloroacetate are used as starting substances for process (e) according to the invention, the course of the reaction can be represented by the following equation:

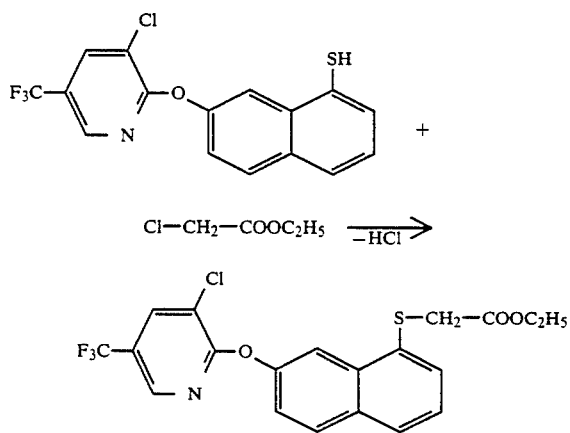

Formula (II) provides a general definition of the halogeno-(hetero)aryl compounds to be used as starting substances in process (a) according to the invention for the preparation of compounds of the formula (I).

In formula (II), $R^1$, $R^2$, $R^3$, $R^4$ and X preferably or in particular have those meanings which have already been mentioned above as preferred or as particularly preferred for $R^1$, $R^2$, $R^3$, $R^4$ and X in connection with the description of the compounds of the formula (I) according to the invention, and $Z^1$ preferably represents fluorine or chlorine.

Examples which may be mentioned of the starting substances of the formula (II) are: 4-chloro-benzotrifluoride, 3,4-dichloro-benzotrifluoride, 3,4,5-trichloro-benzotrifluoride, 3,4-dichloro-5-fluorobenzotrifluoride, 2,3,4,5-tetrachloro-benzotrifluoride, 3,5-dichloro-2,4-difluoro-benzotrifluoride, 3-chloro-4,5-difluoro-benzotrifluoride and 2,3,5-trichloro-pyridine.

The compounds of the formula (II) are known and/or can be prepared by processes which are in themselves known (compare J. Chem. Soc. 1969, 211-217 -ibid. 1971, 1547-1549; EP-A No. 34,402; U.S. Pat. No. 4,424,396; EP-A No. 145,314; and FR-A No. 2,538,380 (Chem. Abstracts 102 (1985), 61914x)).

Examples which may be mentioned of the hydroxynaphthalanesulphonic acids of the formula (III) and their salts which are furthermore to be used as starting substances in process (a) are:

6-hydroxy-naphthalene-2-sulphonic acid and its sodium an potassium salts, 7-hydroxy-naphthalene-2-sulphonic acid and its sodium and potassium salts, 7-hydroxy-naphthalene1-sulphonic acid and its sodium and potassium salts, 6-hydroxy-naphthalene-1-sulphonic acid and its sodium and potassium salts and 5-hydroxy-naphthalene-1-sulphonic acid and its sodium and potassium salts.

The hydroxynaphthalenesulphonic acids of the formula (III) are known organic synthesis chemicals.

Process (a) according to the invention for the preparation of the new compounds of the formula (I) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and dimethyl sulphoxide, tetramethylene sulphone and hexamethylphosphoric acid triamide.

Aprotic polar organic solvents, such as, for example, acetone, acetonitrile, methyl ethyl ketone, propionitrile, dimethylformamide, dimethylacetamide, dimethyl sulphoxide, sulpholane and N-methylpyrrolidone, are particularly preferred.

All the acid-binding agents which can usually be employed for such reactions can be used as acid acceptors in process (a) according to the invention. Preferred possible acid-binding agents are alkali metal hydroxides, such as, for example, sodium hydroxide and potassium hydroxide, alkaline earth metal hydroxides, such as, for example, calcium hydroxide, alkali metal carbonates and alcoholates, such as sodium carbonate and potassium carbonate and sodium tert.-butylate and potassium tert.-butylate, and furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

The reaction temperatures can be varied within a substantial range in process (a) according to the invention. In general, the reaction is carried out at temperatures between 0° C. and 200° C., preferably at temperatures between 20° C. and 150° C.

Process (a) according to the invention is in general carried out under normal pressure. However, it is also possible for the process to be carried out under increased or reduced pressure.

For carrying out process (a) according to the invention, the particular starting substances required are in general employed in approximately equimolar amounts. However, it is also possible for one of the two particular components employed to be used in a larger excess. The reactions are in general carried out in a suitable diluent in the presence of an acid acceptor, and the reaction mixture is stirred at the particular required temperature for several hours. Working up in process (a) according to the invention is in each case carried out by customary methods.

The products which are in general initially obtained as metal salts in process (a) can be converted into the corresponding free acids by treatment with strong acids, such as, for example, hydrochloric acid or sulphuric acid.

Formula (I) provides a general definition of the compounds to be used as starting substances in process (b) according to the invention, with the proviso that n represents the number 1, Y represents oxygen and Z represents hydrogen or a metal equivalent. In this case, m, $R^1$, $R^2$, $R^3$, $R^4$ and X preferably or in particular have those meanings which have already been mentioned above as preferred or as particularly preferred in the context of the description of the compounds of the formula (I) according to the invention, and Z preferably represents hydrogen, sodium or potassium.

Examples of the starting substances for process (b) are shown in the following Table 1.

TABLE 1

Examples of the starting substances for process (b)

(I)

In this formula, in each individual case:
n = 1, Y = oxygen

| m | $R^1$ | $R^2$ | $R^3$ | $R^4$ | X | Z |
|---|---|---|---|---|---|---|
| 0 | Cl | H | Cl | H | CH | H |
| 1 | Cl | H | Cl | H | CH | H |
| 2 | Cl | H | Cl | H | CH | H |
| 0 | Cl | H | Cl | H | N | H |
| 1 | Cl | H | Cl | H | N | H |
| 2 | Cl | H | Cl | H | N | H |
| 0 | Cl | H | CF$_3$ | H | CH | H |
| 1 | Cl | H | CH$_3$ | H | CH | H |
| 2 | Cl | H | CF$_3$ | H | CH | H |
| 0 | Cl | H | CF$_3$ | H | N | H |
| 1 | Cl | H | CF$_3$ | H | N | H |
| 2 | Cl | H | CF$_3$ | H | N | H |
| 0 | Cl | H | CF$_3$ | H | C—Cl | H |
| 1 | Cl | H | CF$_3$ | H | C—Cl | H |
| 2 | Cl | H | CF$_3$ | H | C—Cl | H |
| 0 | Cl | H | CF$_3$ | H | C—F | H |
| 1 | Cl | H | CF$_3$ | H | C—F | H |
| 2 | Cl | H | CF$_3$ | H | C—F | H |
| 0 | Cl | H | CF$_3$ | F | C—Cl | H |
| 1 | Cl | H | CF$_3$ | F | C—Cl | H |
| 2 | Cl | H | CF$_3$ | F | C—Cl | H |
| 0 | Cl | H | CF$_3$ | Cl | C—Cl | H |
| 1 | Cl | H | CF$_3$ | Cl | C—Cl | H |
| 2 | Cl | H | CF$_3$ | Cl | C—Cl | H |
| 0 | Cl | H | SO$_2$CF$_3$ | H | CH | H |
| 1 | Cl | H | SO$_2$CF$_3$ | H | CH | H |
| 2 | Cl | H | SO$_2$CF$_3$ | H | CH | H |
| 0 | Cl | H | SO$_2$CF$_3$ | H | C—Cl | H |
| 1 | Cl | H | SO$_2$CF$_3$ | H | C—Cl | H |
| 2 | Cl | H | SO$_2$CF$_3$ | H | C—Cl | H |
| 0 | Cl | H | SO$_2$CF$_3$ | H | C—F | H |
| 1 | Cl | H | SO$_2$CF$_3$ | H | C—F | H |
| 2 | Cl | H | SO$_2$CF$_3$ | H | C—F | H |
| 0 | CN | H | CF$_3$ | H | CH | H |
| 1 | CN | H | CF$_3$ | H | CH | H |
| 2 | CN | H | CF$_3$ | H | CH | H |

TABLE 1-continued

Examples of the starting substances for process (b)

The examples shown in Table 1 specifically apply in each case to the especially preferred groups of compounds of the formula (I) which are outlined above by the formulae (Ia), (Ib), (Ic), (Id) and (Ie). The starting substances of the formula (I) described above for process (b) are new compounds according to the invention; they can be prepared by processes (a) or (c) according to the invention.

Process (b) according to the invention is carried out using a halogenating agent. In the case where m represents the number 0, suitable halogenating agents are, in particular, elemental halogens, such as, for example, chlorine or bromine, and in the case where m represents the numbers 1 or 2, suitable halogenating agents are furthermore also acid halides, such as, for example, phosgene, thionyl chloride, chlorosulphonic acid, phosphoryl chloride, phosphorus(III) chloride, phosphorus-(III) bromide and phosphorus(V) chloride.

The substances which are usually employed for the preparation of acid halides, such as, for example, pyridine, dimethylformamide, trimethylphosphine oxide, triphenylphosphine or phosphorus oxychloride, can be used as catalysts or halogenating auxiliaries for carrying out process (b) according to the invention.

If appropriate, process (b) according to the invention is carried out in the presence of a diluent. Preferred possible diluents are relatively inert organic solvents from the series comprising halogenated hydrocarbons, such as, for example, methylene chloride, chloroform, carbon tetrachloride, 1,2-dichloroethane, chlorobenzene or 1,2-dichlorobenzene.

The reaction temperatures can be varied within a substantial range in process (b) according to the invention. The reaction is in general carried out at temperatures between 0° C. and 100° C., preferably at temperatures between 10° C. and 90° C.

Process (b) according to the invention is in general carried out under normal pressure. However, it is also possible for the process to be carried out under increased or reduced pressure.

For carrying out process (b) according to the invention, in general between 1 and 50 mol, preferably between 1.5 and 20 mol, of halogenating agent are used per mol of starting compound of the formula (I). The reaction components are in general brought together at room temperature and the reaction mixture is stirred, if appropriate at elevated temperature, until the reaction has ended. In process (b), the reaction products are in general obtained in crystalline form after concentration and dilution of the residue with water, and they can be isolated by filtration with suction.

Formula (I) provides a general definition of the compounds to be used as starting substances in process (c) according to the invention, with the proviso that m represents the number 2, n represents the number 0 and Z represents halogen. In this case, $R^1$, $R^2$, $R^3$, $R^4$ and X preferably or in particular have those meanings which have already been given above as preferred or as particularly preferred in the context of the description of the compounds of the formula (I) according to the invention, and Z preferably represents chlorine.

Examples of the starting substances for process (c) are shown in the following Table 2.

TABLE 2

Examples of the starting substances for process (c)

$$R^2 \underset{R^4}{\overset{R^1}{\underset{X}{\bigcirc}}} R^3 - O - \bigcirc\bigcirc - S(O)_m - (Y)_n - Z \quad (I)$$

In this formula, in each individual case:
m = 2, n = 0

| $R^1$ | $R^2$ | $R^3$ | $R^4$ | X | Z |
|---|---|---|---|---|---|
| Cl | H | Cl | H | CH | Cl |
| Cl | H | Cl | H | N | Cl |
| Cl | H | $CF_3$ | H | CH | Cl |
| Cl | H | $CF_3$ | H | N | Cl |
| Cl | H | $CF_3$ | H | C-Cl | Cl |
| Cl | H | $CF_3$ | H | C-F | Cl |
| Cl | H | $CF_3$ | F | C-Cl | Cl |
| Cl | H | $CF_3$ | Cl | C-Cl | Cl |
| F | H | $CF_3$ | H | C-F | Cl |
| Cl | H | $SO_2CF_3$ | H | CH | Cl |
| Cl | H | $SO_2CF_3$ | H | C-Cl | Cl |
| CN | H | $CF_3$ | H | CH | Cl |

The examples shown in Table 2 specifically apply in each case to the especially preferred groups of compounds of the formula (I) which are outlined above by the formulae (Ia), (Ib), (Ic), (Id) and (Ie).

The starting substances of the formula (I) described above for process (c) are new compounds according to the invention; they can be prepared by process (b) according to the invention.

Process (c) according to the invention is carried out using a reducing agent. Possible reducing agents are the customary substances which are suitable for reduction of sulphonic acid halides, such as, for example, zinc, hydrogen sulphide or sodium sulphite.

Reduction auxiliaries which may be mentioned and which are to be employed, if appropriate, depending on the reducing agent used, are acids, such as, for example, hydrochloric acid, sulphuric acid and acetic acid, and bases, such as, for example, sodium hydroxide solution and potassium hydroxide solution.

Process (c) according to the invention is preferably carried out using diluents. Possible diluents are, in addition to water, virtually all the inert organic solvents, such as are mentioned above for process (a) according to the invention. Water-miscible organic solvents, such as, for example, dioxane and dimethylformamide, are particularly suitable.

The reaction temperatures can be varied within a substantial range in process (c) according to the invention. The reaction is in general carried out at temperatures between 0° C. and 150° C., preferably at temperatures between 10° C. and Process (c) according to the invention is in general carried out under normal pressure. However, it is also possible for the process to be carried out under increased or reduced pressure.

For carrying out process (c) according to the invention, in general between 1 and 20 mol, preferably between 1 and 10 mol, of reducing agent are employed per mol of starting compound of the formula (I). The reaction components are in general brought together at room temperature or at a slightly increased or reduced temperature and the reaction mixture is stirred, if appropriate at elevated temperature, until the reaction has ended. Working up can be carried out by customary methods.

Formula (I) provides a general definition of the compounds to be used as starting substances in process (d) according to the invention, with the proviso that n represents the number 0 and Z represents halogen.

In this case, m, $R^1$, $R^2$, $R^3$, $R^4$ and X preferably or in particular have those meanings which have already been given above as preferred or as particularly preferred in the context of the description of the compounds of the formula (I) according to the invention, and Z preferably represents chlorine.

Examples of the starting substances of the formula (I) for process (d) are shown in the following Table 3.

TABLE 3

Examples of the starting substances for process (d)

$$R^2 \underset{R^4}{\overset{R^1}{\underset{X}{\bigcirc}}} R^3 - O - \bigcirc\bigcirc - S(O)_m - (Y)_n - Z \quad (I)$$

In this formula, in each individual case: n = 0

| m | $R^1$ | $R^2$ | $R^3$ | $R^4$ | X | Z |
|---|---|---|---|---|---|---|
| 0 | Cl | H | Cl | H | CH | Cl |
| 1 | Cl | H | Cl | H | CH | Cl |
| 2 | Cl | H | Cl | H | CH | Cl |
| 0 | Cl | H | Cl | H | N | Cl |
| 1 | Cl | H | Cl | H | N | Cl |
| 2 | Cl | H | Cl | H | N | Cl |
| 0 | Cl | H | $CF_3$ | H | CH | Cl |
| 1 | Cl | H | $CF_3$ | H | CH | Cl |
| 2 | Cl | H | $CF_3$ | H | CH | Cl |
| 0 | Cl | H | $CF_3$ | H | N | Cl |
| 1 | Cl | H | $CF_3$ | H | N | Cl |
| 2 | Cl | H | $CF_3$ | H | N | Cl |
| 0 | Cl | H | $CF_3$ | H | C-Cl | Cl |
| 1 | Cl | H | $CF_3$ | H | C-Cl | Cl |
| 2 | Cl | H | $CF_3$ | H | C-Cl | Cl |
| 2 | CN | H | $CF_3$ | H | CH | Cl |
| 0 | Cl | H | $CF_3$ | H | C-F | Cl |
| 1 | Cl | H | $CF_3$ | H | C-F | Cl |
| 2 | Cl | H | $CF_3$ | H | C-F | Cl |
| 0 | Cl | H | $CF_3$ | F | C-Cl | Cl |
| 1 | Cl | H | $CF_3$ | F | C-Cl | Cl |
| 2 | Cl | H | $CF_3$ | F | C-Cl | Cl |
| 0 | Cl | H | $CF_3$ | Cl | C-Cl | Cl |
| 1 | Cl | H | $CF_3$ | Cl | C-Cl | Cl |
| 2 | Cl | H | $CF_3$ | Cl | C-Cl | Cl |
| 0 | Cl | H | $SO_2CF_3$ | H | CH | Cl |
| 1 | Cl | H | $SO_2CF_3$ | H | CH | Cl |
| 2 | Cl | H | $SO_2CF_3$ | H | CH | Cl |
| 0 | Cl | H | $SO_2CF_3$ | H | C-Cl | Cl |
| 1 | Cl | H | $SO_2CF_3$ | H | C-Cl | Cl |
| 2 | Cl | H | $SO_2CF_3$ | H | C-Cl | Cl |

The examples shown in Table 3 specifically apply in each case to the especially preferred groups of compounds of the formula (1) which are outlined above by the formulae (Ia), (Ib), (Ic), (Id) and (Ie).

The starting substances of the formula (I) described above for process (d) are new compounds according to the invention; they can be prepared by process (b) according to the invention.

Formula (IV) provides a general definition of the nucleophilic compounds furthermore to be used as starting substances in process (d) according to the invention.

In formula (IV), n, Y and Z preferably or in particular have those meanings which have already been given above as preferred or as particularly preferred for n, Y and Z in connection with the description of the compounds of the formula (I) according to the invention, and M preferably represents hydrogen, sodium or potassium.

Examples of the starting substances of the formula (IV) are shown in the following Table 4.

TABLE 4

Examples of the starting substances of the formula (IV)
M—(Y)$_n$—Z (IV)

| M | n | Y | Z |
|---|---|---|---|
| H | 1 | O | CH$_3$ |
| Na | 1 | O | CH$_3$ |
| H | 1 | O | C$_2$H$_5$ |
| Na | 1 | O | C$_2$H$_5$ |
| K | 1 | O | C$_2$H$_5$ |
| H | 1 | O | C$_3$H$_7$ |
| H | 1 | O | CH(CH$_3$)$_2$ |
| H | 1 | O | C$_4$H$_9$ |
| H | 1 | NH | H |
| H | 1 | NH | CH$_3$ |
| H | 1 | NH | C$_2$H$_5$ |
| H | 1 | NH | C$_3$H$_7$ |
| H | 1 | NH | CH(CH$_3$)$_2$ |
| H | 1 | NH | C$_4$H$_9$ |
| H | 1 | NH | CH$_2$CH(CH$_3$)$_2$ |
| H | 1 | NH | CH$_2$COOC$_2$H$_5$ |
| H | 1 | NH | CH(CH$_3$)—COOC$_2$H$_5$ |
| H | 1 | NH | CH$_2$CH=CH$_2$ |
| H | 1 | NH | 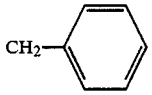 |
| H | 1 | NH | 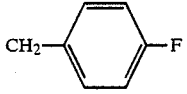 |
| H | 1 | NH | 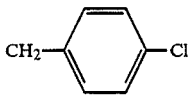 |
| H | 1 | NH |  |
| H | 1 | NH | CH$_2$CH$_2$OCH$_3$ |

TABLE 4-continued

Examples of the starting substances of the formula (IV)
M—(Y)$_n$—Z (IV)

| M | n | Y | Z |
|---|---|---|---|
| H | 1 | NH | 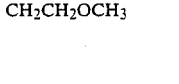 |
| H | 1 | NH | 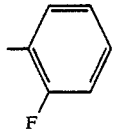 |
| H | 1 | NH | 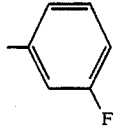 |
| H | 1 | NH | 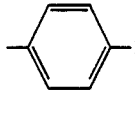 |
| H | 1 | NH | 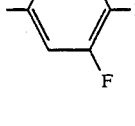 |
| H | 1 | NH | 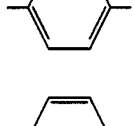 |
| H | 1 | NH | 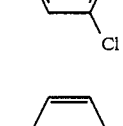 |
| H | 1 | NH | 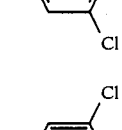 |
| H | 1 | NH | 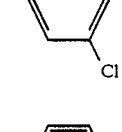 |
| H | 1 | NH | 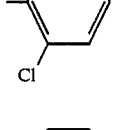 |
| H | 1 | NH | 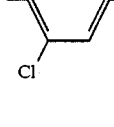 |

TABLE 4-continued

Examples of the starting substances of the formula (IV)

$$M-(Y)_n-Z \quad (IV)$$

| M | n | Y | Z |
|---|---|---|---|
| H | 1 | NH | 2,5-dichlorophenyl |
| H | 1 | NH | 4-bromophenyl |
| H | 1 | NH | 3-nitrophenyl |
| H | 1 | NH | 2-methylphenyl |
| H | 1 | NH | 3-methylphenyl |
| H | 1 | NH | 4-methylphenyl |
| H | 1 | NH | 4-ethylphenyl |
| H | 1 | NH | 4-CF$_3$-phenyl |
| H | 1 | NH | 3-CF$_3$-phenyl |
| H | 1 | NH | 2-CF$_3$-phenyl |
| H | 1 | NH | 4-OCH$_3$-phenyl |
| H | 1 | NH | 3-OCH$_3$-phenyl |
| H | 1 | NH | 2,3-di-OCH$_3$-phenyl |
| H | 1 | NH | 4-OC$_2$H$_5$-phenyl |
| H | 1 | NH | 2-OCHF$_2$-phenyl |
| H | 1 | NH | 4-OCHF$_2$-phenyl |
| H | 1 | NH | 2-OCF$_3$-phenyl |
| H | 1 | NH | 4-OCF$_3$-phenyl |
| H | 1 | NH | 4-SCH$_3$-phenyl |
| H | 1 | NH | 2-SCH$_3$-phenyl |
| H | 1 | NH | 4-SCHF$_2$-phenyl |
| H | 1 | NH | 3-SCHF$_2$-phenyl |

TABLE 4-continued

Examples of the starting substances of the formula (IV)

$$M-(Y)_n-Z \quad (IV)$$

| M | n | Y | Z |
|---|---|---|---|
| H | 1 | NH | -C₆H₄-SCF₃ (para) |
| H | 1 | NH | -C₆H₄-SCF₂Cl (para) |
| H | 1 | NH | -C₆H₄-SO₂CH₃ (para) |
| H | 1 | NH | -C₆H₄-SO₂N(CH₃)₂ (para) |
| H | 1 | NH | -C₆H₄-COOCH₃ (para) |
| H | 1 | NH | -C₆H₄-COOCH₃ (ortho) |
| H | 1 | NH | -C₆H₄-COOC₂H₅ (para) |
| H | 1 | NH | -C₆H₄-COOC₂H₅ (ortho) |
| H | 1 | NHCO | H |
| H | 1 | NHCO | CH₃ |
| H | 1 | NHCO | C₂H₅ |
| H | 1 | NHCO | C₃H₇ |
| H | 1 | NHCO | C₄H₉ |
| H | 1 | NHCO | CH₂—C₆H₅ |
| H | 1 | NHCO | C₆H₅ |
| H | 1 | NHCOO | CH₃ |
| H | 1 | NHCOO | C₂H₅ |
| H | 1 | NHCOO | C₃H₇ |
| H | 1 | NHCOO | C₄H₉ |
| H | 1 | NHCOO | CH₂—C₆H₅ |
| H | 1 | NHCOO | C₆H₅ |
| H | 1 | NHSO₂ | CH₃ |
| H | 1 | NHSO₂ | C₂H₅ |
| H | 1 | NHSO₂ | C₃H₇ |
| H | 1 | NHSO₂ | C₄H₉ |
| H | 1 | NHSO₂ | CH₂Cl |
| H | 1 | NHCO | CH₂Cl |
| H | 1 | NHSO₂ | CH₂CH₂Cl |
| H | 1 | NHCO | CH₂CH₂Cl |
| H | 1 | NHCO | CHCl₂ |
| H | 1 | NHSO₂ | C₆H₅ |
| H | 1 | NHSO₂ | -C₆H₄-Cl (para) |
| H | 1 | NHSO₂ | -C₆H₄-CH₃ (para) |
| H | 0 | — | pyrazol-1-yl |
| K | 0 | — | pyrazol-1-yl |
| H | 0 | — | 3-methylpyrazol-1-yl |
| H | 0 | — | 3,5-dimethylpyrazol-1-yl |
| H | 0 | — | 3,4,5-trimethylpyrazol-1-yl |

TABLE 4-continued

Examples of the starting substances of the formula (IV)

$$M-(Y)_n-Z \quad (IV)$$

| M | n | Y | Z |
|---|---|---|---|
| H | 0 | — | 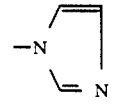 |
| H | 0 | — | 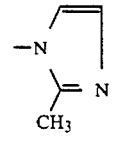 |
| H | 0 | — | 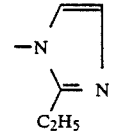 |
| H | 0 | — | 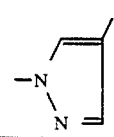 |

The starting substances of the formula (IV) are known synthesis chemicals.

Process (d) according to the invention is preferably carried out using diluents. Possible diluents are, in addition to water, virtually all the inert organic solvents, such as are mentioned above for process (a) according to the invention.

If appropriate, process (d) is carried out in the presence of an acid acceptor. Those acid-binding agents which are mentioned above for process (a), but in particular the aliphatic, aromatic or heterocyclic amines mentioned there, are above all possible.

The reaction temperatures can be varied within a substantial range in process (d) according to the invention.

The reaction is in general carried out at temperatures between −20° C. and +100° C., preferably at temperatures between 0° C. and +80° C. Process (d) according to the invention is in general carried out under normal pressure. However, it is also possible for the process to be carried out under increased or reduced pressure.

For carrying out process (d) according to the invention, the particular starting substances required are in general employed in approximately equimolar amounts. However, it is also possible for one of the two particular components employed to be used in a larger excess. The reactions are in general carried out in a suitable diluent in the presence of an acid acceptor, and the reaction mixture is stirred at the particular required temperature for several hours. Working up in process (d) according to the invention is in each case carried out by customary methods.

Formula (I) provides a general definition of the compounds to be used as starting substances in process (e) according to the invention, with the proviso that Y represents oxygen, sulphur or NH and Z represents hydrogen. In this case, m, n, $R^1$, $R^2$, $R^3$, $R^4$ and X preferably or in particular have those meanings which have already been given above as preferred or as particularly preferred in the context of the description of the compounds of the formula (I) according to the invention, and Y preferably represents NH.

Examples of the starting substances of the formula (I) for process (e) are shown in the following Table 5.

TABLE 5

Examples of the starting substances for process (e)

$$\text{(I)}$$

In this formula, in each individual cases: Z = H

| m | n | $R^1$ | $R^2$ | $R^3$ | $R^4$ | X | Y |
|---|---|---|---|---|---|---|---|
| 0 | 0 | Cl | H | Cl | H | CH | — |
| 1 | 1 | Cl | H | Cl | H | CH | NH |
| 2 | 1 | Cl | H | Cl | H | CH | NH |
| 2 | 0 | Cl | H | Cl | H | CH | — |
| 0 | 0 | Cl | H | Cl | H | N | — |
| 1 | 1 | Cl | H | Cl | H | N | NH |
| 2 | 1 | Cl | H | Cl | H | N | NH |
| 2 | 0 | Cl | H | Cl | H | N | — |
| 0 | 0 | Cl | H | $CF_3$ | H | CH | — |
| 1 | 1 | Cl | H | $CF_3$ | H | CH | NH |
| 2 | 1 | Cl | H | $CF_3$ | H | CH | NH |
| 2 | 0 | Cl | H | $CF_3$ | H | CH | — |
| 0 | 0 | Cl | H | $CF_3$ | H | N | — |
| 1 | 1 | Cl | H | $CF_3$ | H | N | NH |
| 2 | 1 | Cl | H | $CF_3$ | H | N | NH |
| 2 | 0 | Cl | H | $CF_3$ | H | N | — |
| 0 | 0 | Cl | H | $CF_3$ | H | C—Cl | — |
| 1 | 1 | Cl | H | $CF_3$ | H | C—Cl | NH |
| 2 | 1 | Cl | H | $CF_3$ | H | C—Cl | NH |
| 2 | 0 | Cl | H | $CF_3$ | H | C—Cl | — |
| 0 | 0 | Cl | H | $CF_3$ | H | C—F | — |
| 1 | 1 | Cl | H | $CF_3$ | H | C—F | NH |
| 2 | 1 | Cl | H | $CF_3$ | H | C—F | NH |
| 2 | 0 | Cl | H | $CF_3$ | H | C—F | — |
| 0 | 0 | Cl | H | $CF_3$ | F | C—Cl | — |
| 1 | 1 | Cl | H | $CF_3$ | F | C—Cl | NH |
| 2 | 1 | Cl | H | $CF_3$ | F | C—Cl | NH |
| 2 | 0 | Cl | H | $CF_3$ | F | C—Cl | — |
| 0 | 0 | Cl | H | $CF_3$ | Cl | C—Cl | — |
| 1 | 1 | Cl | H | $CF_3$ | Cl | C—Cl | NH |
| 2 | 1 | Cl | H | $CF_3$ | Cl | C—Cl | NH |
| 2 | 0 | Cl | H | $CF_3$ | Cl | C—Cl | — |
| 2 | 1 | CN | H | $CF_3$ | H | CH | NH |
| 0 | 0 | Cl | H | $SO_2CF_3$ | H | CH | — |
| 1 | 1 | Cl | H | $SO_2CF_3$ | H | CH | NH |
| 2 | 1 | Cl | H | $SO_2CF_3$ | H | CH | NH |
| 2 | 0 | Cl | H | $SO_2CF_3$ | H | CH | — |
| 0 | 0 | Cl | H | $SO_2CF_3$ | H | C—Cl | — |
| 1 | 1 | Cl | H | $SO_2CF_3$ | H | C—Cl | NH |
| 2 | 1 | Cl | H | $SO_2CF_3$ | H | C—Cl | NH |
| 2 | 0 | Cl | H | $SO_2CF_3$ | H | C—Cl | — |

The examples shown in Table 5 specifically apply in each case to the especially preferred groups of compounds of the formula (I) which are outlined above by the formulae (Ia), (Ib), (Ic), (Id) and (Ie).

The starting substances of the formula (I) described above for process (e) are new compounds according to the invention; they can be prepared by processes (c) and (d) according to the invention.

Formula (V) provides a general definition of the electrophilic compounds furthermore to be used as starting substances in process (e) according to the invention.

In formula (V), n and $Z^3$ preferably or in particular have those meanings which have already been given above as preferred or as particularly preferred for n and Z in connection with the description of the compounds of the formula (I) according to the invention, and $Z^2$ preferably represents chlorine or bromine; $Y^1$ represents CO or $SO_2$.

Examples of the starting substances of the formula (V) are shown in the following Table 6.

TABLE 6

Examples of the starting substances of the formula (V)

$$Z^2-(Y^1)_n-Z^3 \quad (v)$$

| $Z^2$ | $Y^1$ | n | $Z^3$ |
|---|---|---|---|
| Br | — | 0 | $CH_3$ |
| Br | — | 0 | $C_2H_5$ |
| Br | — | 0 | $C_3H_7$ |
| Br | — | 0 | $CH(CH_3)_2$ |
| Br | — | 0 | $C_4H_9$ |
| Br | — | 0 | $CH_2CH(CH_3)_2$ |
| Cl | — | 0 | $CHF_2$ |
| Br | — | 0 | $CH_2CH_2CH_2Cl$ |
| Br | — | 0 | $CH_2CH=CH_2$ |
| Cl | — | 0 | $CH_2COOCH_3$ |
| Br | — | 0 | $CH_2COOCH_3$ |
| Cl | — | 0 | $CH_2COOC_2H_5$ |
| Br | — | 0 | $CH_2COOC_2H_5$ |
| Cl | — | 0 | $\underset{CH_3}{CHCOOCH_3}$ |
| Br | — | 0 | $\underset{CH_3}{CHCOOCH_3}$ |
| Cl | — | 0 | $\underset{CH_3}{CHCOOC_2H_5}$ |
| Br | — | 0 | $\underset{CH_3}{CHCOOC_2H_5}$ |
| Br | — | 0 | $CH_2CH_2COOCH_3$ |
| Br | — | 0 | $CH_2CH_2COOC_2H_5$ |
| Cl | — | 0 | 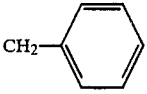 |
| Cl | — | 0 |  |
| Cl | — | 0 |  |
| Cl | CO | 1 | $CH_3$ |
| Cl | CO | 1 | $C_2H_5$ |
| Cl | CO | 1 | $C_3H_7$ |
| Cl | CO | 1 | $CH(CH_3)_2$ |
| Cl | CO | 1 | $CH_2Cl$ |
| Cl | CO | 1 | $CHCl_2$ |
| Cl | CO | 1 | $CCl_3$ |
| Cl | CO | 1 | 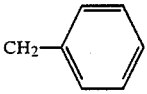 |

TABLE 6-continued

Examples of the starting substances of the formula (V)

$$Z^2-(Y^1)_n-Z^3 \quad (v)$$

| $Z^2$ | $Y^1$ | n | $Z^3$ |
|---|---|---|---|
| Cl | CO | 1 |  |
| Cl | CO | 1 | 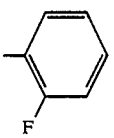 |
| Cl | CO | 1 | 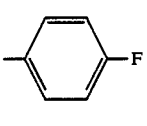 |
| Cl | CO | 1 | 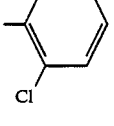 |
| Cl | CO | 1 | 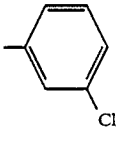 |
| Cl | CO | 1 | 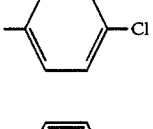 |
| Cl | CO | 1 | 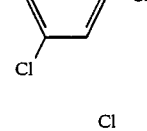 |
| Cl | CO | 1 | 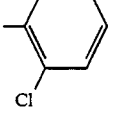 |
| Cl | CO | 1 | 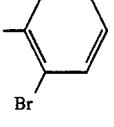 |
| Cl | CO | 1 | 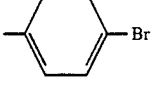 |

TABLE 6-continued

Examples of the starting substances of the formula (V)

$Z^2-(Y^1)_n-Z^3$

| $Z^2$ | $Y^1$ | n | $Z^3$ |
|---|---|---|---|
| Cl | CO | 1 | 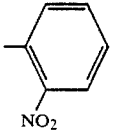 (2-NO$_2$-phenyl) |
| Cl | CO | 1 | 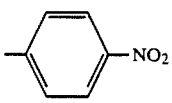 (4-NO$_2$-phenyl) |
| Cl | CO | 1 | 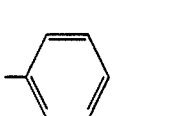 (2-CH$_3$-phenyl) |
| Cl | CO | 1 | 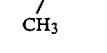 (4-CH$_3$-phenyl) |
| Cl | SO$_2$ | 1 | CH$_3$ |
| Cl | SO$_2$ | 1 | C$_2$H$_5$ |
| Cl | SO$_2$ | 1 | C$_3$H$_7$ |
| Cl | SO$_2$ | 1 | C$_4$H$_9$ |
| Cl | SO$_2$ | 1 | CH$_2$Cl |
| Cl | SO$_2$ | 1 | CH$_2$CH$_2$Cl |
| Cl | SO$_2$ | 1 | 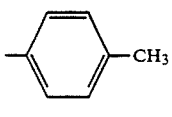 (phenyl) |
| Cl | SO$_2$ | 1 | 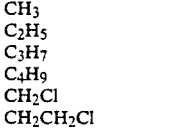 (4-Cl-phenyl) |
| Cl | SO$_2$ | 1 | 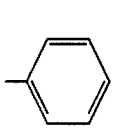 (3-Cl-phenyl) |
| Cl | SO$_2$ | 1 | 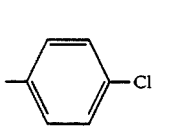 (2,5-Cl$_2$-phenyl) |
| Cl | SO$_2$ | 1 | 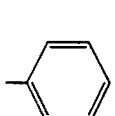 (3-F-phenyl) |
| Cl | SO$_2$ | 1 | 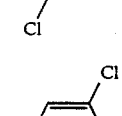 (4-F-phenyl) |
| Cl | SO$_2$ | 1 | 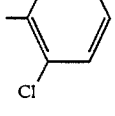 (2-Br-phenyl) |
| Cl | SO$_2$ | 1 | 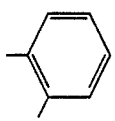 (4-NO$_2$-phenyl) |
| Cl | SO$_2$ | 1 | 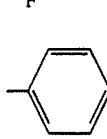 (2-NO$_2$-phenyl) |
| Cl | SO$_2$ | 1 | 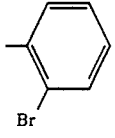 (4-CH$_3$-phenyl) |
| Cl | SO$_2$ | 1 | 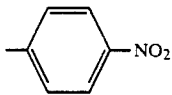 (2-CH$_3$-phenyl) |
| Cl | SO$_2$ | 1 | 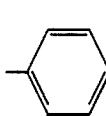 (2-CF$_3$-phenyl) |
| Cl | SO$_2$ | 1 | 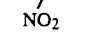 (2-OCHF$_2$-phenyl) |
| Cl | SO$_2$ | 1 | 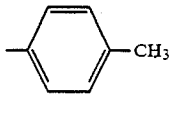 (2-OCF$_3$-phenyl) |
| Cl | SO$_2$ | 1 | 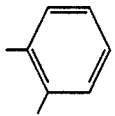 (2-COOCH$_3$-phenyl) |

The starting substances of the formula (V) are known organic synthesis chemicals. Process (e) according to the invention is preferably carried out using diluents. Possible diluents are, in addition to water, virtually all the inert organic solvents, such as are mentioned above for process (a) according to the invention.

If appropriate, process (e) is carried out in the presence of an acid acceptor. Those acid-binding agents which are mentioned above for process (a), but in particular the aliphatic, aromatic or heterocyclic amines mentioned there, are above all possible.

The reaction temperatures can be varied within a substantial range in process (e) according to the invention. The reaction is in general carried out at temperatures between −20° C. and +100° C., preferably at temperatures between 0° C. and +80° C.

Process (e) according to the invention is in general carried out under normal pressure. However, it is also possible for the process to be carried out under increased or reduced pressure.

For carrying out process (e) according to the invention, the particular starting substances required are in general employed in approximately equimolar amounts. However, it is also possible for one of the two particular components employed to be used in a larger excess. The reactions are in general carried out in a suitable diluent in the presence of an acid acceptor, and the reaction mixture is stirred at the particular required temperature for several hours. Working up in process (e) according to the invention is in each case carried out by customary methods.

If appropriate, salts can be prepared from the compounds of the general formula (I) according to the invention. Such salts are obtained in a simple manner by customary salt formation methods, for example by dissolving or dispersing a compound of the formula (I) in a suitable solvent, such as, for example, water, methanol, ethanol or acetone, and adding a suitable base. The salts can then be isolated - if appropriate after prolonged stirring - by concentration or filtration with suction. In individual cases (compare Preparation Example 1), salts of compounds of the formula (I) are obtained directly when carrying out the preparation process according to the invention.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selectively combating dicotyledon weeds in monocotyledon and dicotyledon crops, above all by the post-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/ or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolyzates; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethyl- propyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5(4H)-one (METRIBUZIN) for combating weeds in soya beans; and furthermore also 2,4-dichlorophenoxyacetic acid (2,4-D); 4-(2,4-dichlorophenoxy)butyric acid (2,4-DB); 2,4-dichlorophenoxypropionic acid (2,4-DP); 2-chloro-4-ethylamino-6-isopropylamino-1,3,5-triazine (ATRAZIN); 3-isopropyl-2,1,3-benzothiadiazin-4-one 2,2-dioxide (BENTAZON); methyl 5-(2,4-dichlorophenoxy)-2-nitrobenzoate (BIFENOX); 3,5-dibromo-4-hydroxybenzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)urea (CHLORTOLURON); [(4-amino-3,5-dichloro-6-fluoro-2-pyridinyl)-oxy]-acetic acid and its 1-methylheptyl ester (FLUROXYPYR); methyl 2-[4,5-dihydro-4-methyl-4-(1-methyl-ethyl)-5-oxo-1H-imidazol-2-yl]-4(5)-methyl-benzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-{[[((4-methoxy-6-methyl-1,3,5-triazin-2-yl)-amino)-carbonyl]amino]-sulphonyl}-benzoic acid or its methyl ester (METSULFURON); N-(1-ethylpropyl)-3,4-dimethyl-2,6-dinitroaniline (PENDIMETHALIN); 0-(6-chloro-3-phenyl-pyridazin-4-yl) S-octyl thiocarbonate (PYRIDATE); 4-ethylamino-2-t-butylamino-6-methylthio-s-triazine (TERBUTRYNE); and methyl 3-1[[[(4-methoxy-6-methyl-1,3,5-triazin-2-yl)amino]-carbonyl]-amino]-sulphonyl]-thiophene-2-carboxylate (THIAMETURON). Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

EXAMPLE 1

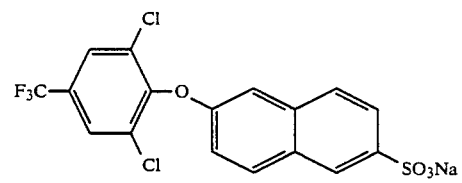

[Process (a)]

124 g (0.5 mol) of 3,4,5-trichlorobenzotrifluoride are added to a mixture of 135 g (0.5 mol) of sodium 6-hydroxynaphthalene-2-sulphonate, 30 g (0.54 mol) of potassium hydroxide powder and 1,000 ml of dimethyl sulphoxide, while stirring, and the reaction mixture is stirred first at 60° C. for 3 hours and then at 20° C. for 15 hours. After concentration, the residue is digested with water and the product obtained as crystals is isolated by filtration with suction. 209.5 g (91% of theory) of sodium 6-(2,6-dichloro-4-trifluoromethyl-phenoxy)-naphthalene-2-sulphonate, which melts above 310° C. with decomposition, are obtained.

EXAMPLE 2

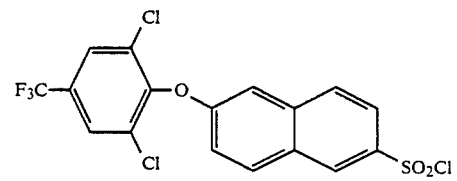

[Process (b)]

A mixture of 2.3 g (5.0 mmol) of sodium 6-(2,6-dichloro-4-trifluoromethyl-phenoxy)-naphthalene-2-sulphonate, 1.6 g (7.5 mmol) of phosphorus(V) chloride and 15 ml of phosphoryl chloride is stirred first at 70° C. for 6 hours and then at 20° C. for 15 hours, and is then poured into water and stirred for a further hour. The product obtained as crystals is isolated by filtration with suction.

1.8 g (79% of theory) of 6-(2,6-dichloro-4-tri-fluoromethyl-phenoxy)-naphthalene-2-sulphonyl chloride of melting point 140° C. are obtained.

EXAMPLE 3

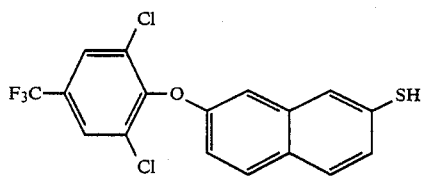

[Process (c)]

12.5 g (0.025 mol) of 7-(2,6-dichloro-4-trifluoromethyl-phenoxy)-naphthalene-2-sulphonyl chloride and 25 ml of concentrated hydrochloric acid are added successively with stirring to a mixture of 12.5 g (0.19 mol) of zinc dust and 100 ml of dioxane. The reaction mixture is heated to the boiling point under reflux for 5 hours and then stirred for a further 15 hours at 20° C. After concentration, the residue is taken up in methylene chloride/water, the solution is filtered, the filtrate is shaken, and the organic phase is separated off, washed with water, dried with sodium sulphate and filtered.

The filtrate is concentrated, the residue is digested with ethanol and the product which is obtained here as crystals is isolated by filtration with suction.

4.8 g (49% of theory) of 7-(2,6-dichloro-4-trifluoromethylphenoxy)-naphthalene-2-thiol of melting point 98° C. are obtained.

EXAMPLE 4

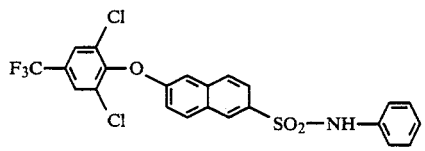

[Process (d)]

A mixture of 4.6 g (0.01 mol) of 6-(2,6-dichloro-4-trifluoromethyl-phenoxy)-naphthalene-2-sulphonyl chloride, 0.9 g (0.01 mol) of aniline, 1.1 g (0.011 mol) of triethylamine and 100 ml of acetonitrile is stirred at 20° C. for 15 hours. The product obtained as crystals on subsequent dilution with water is isolated by filtration with suction.

3.0 g (59% of theory) of 6-(2,6-dichloro-4-trifluoromethyl-phenoxy)-naphthalene-2-sulphanilide of melting point 174° C. are obtained.

EXAMPLE 5

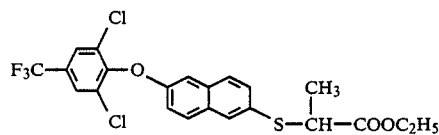

[Process (e)]

A mixture of 1.9 g (5 mmol) of 6-(2,6-dichloro-4-trifluoromethyl-phenoxy)-naphthalene-2-thiol, 1.0 g (5.5 mmol) of ethyl α-bromo-propionate, 0.7 g (5.5 mmol) of potassium carbonate and 50 ml of acetonitrile is heated at the boiling point under reflux for 15 hours and then concentrated. The residue is taken up in methylene chloride, and the solution is washed twice with water, dried with sodium sulphate and filtered. The solvent is distilled off carefully from the filtrate under 1 mm Hg (0.13 kPa).

1.4 g (57% of theory) of ethyl α-[6-(2,6-dichloro-4-trifluoromethyl-phenoxy)-naphthalen-2-yl-thio]-propionate are obtained as an oily residue.

NMR data :*)
$^1$H-NMR (CDCl$_3$, δ): 3.8 ppm

*) The $^1$H-NMR spectra were recorded in deuterochloro-form (CDCl$_3$) using tetramethylsilane (TMS) as the internal standard. The chemical shift is stated as the δ value in ppm.

EXAMPLE 6

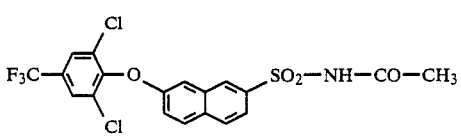

[Process (e)]

A mixture of 2.1 g (5.0 mmol) of 7-(2,6-dichloro-4-trifluoromethyl-phenoxy)-naphthalene-2-sulphonamide, 0.4 g (5.5 mmol) of acetyl chloride, 1.1 g (5.5 mmol) of potassium carbonate and 50 ml of acetone is heated at the boiling point under reflux for 15 hours. After addition of methylene chloride, the mixture is washed with water, dried with sodium sulphate and filtered. The solvent is distilled off from the filtrate, the residue is digested with ethanol and the product obtained here as crystals is isolated by filtration with suction.

1.1 g (46% of theory) of N-acetyl-7-(2,6-dichloro-4-trifluoromethyl-phenoxy)-naphthalene-2-sulphonamide of melting point 137° C. are obtained.

The compounds of the formula (I) listed in the following Table 7 - specified more precisely by the "isomer groups" of the formulae (Ia), (Ib), (Ic), (Id) and (Ie) - can be prepared analogously to Examples 1 to 6 and in accordance with the general description of the preparation processes according to the invention.

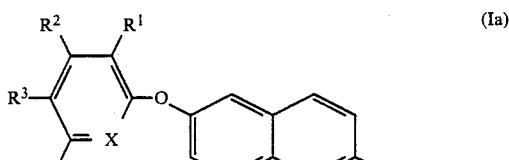

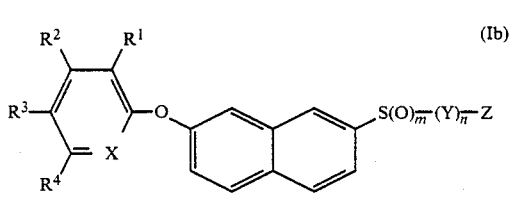

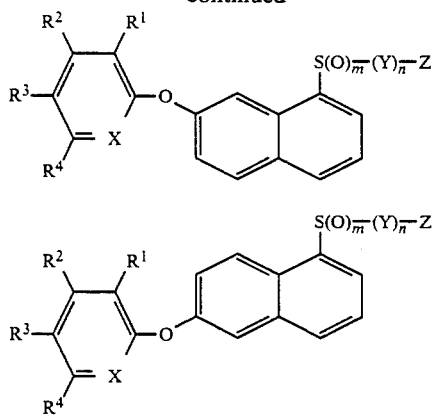

(Ic)

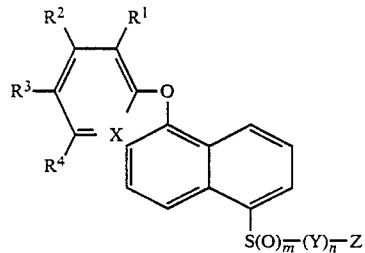

(Ie)

(Id)

TABLE 7
Examples of the compounds of the formula (I)

| Example No. | Isomer group | m | n | R¹ | R² | R³ | R⁴ | X | Y | Z | Physical data |
|---|---|---|---|---|---|---|---|---|---|---|---|
| 7 | Ia | 0 | 0 | Cl | H | CF₃ | H | C—Cl | — | H | m.p.: 129° C. |
| 8 | Ib | 2 | 1 | Cl | H | CF₃ | H | C—Cl | O | Na | m.p.: 262° C. |
| 9 | Ib | 2 | 0 | Cl | H | CF₃ | H | C—Cl | — | Cl | m.p.: 176° C. |
| 10 | Ia | 2 | 1 | Cl | H | CF₃ | H | C—Cl | NH | H | m.p.: 204° C. |
| 11 | Ib | 2 | 1 | Cl | H | CF₃ | H | C—Cl | O | C₂H₅ | m.p.: 105° C. |
| 12 | Ib | 2 | 1 | Cl | H | CF₃ | H | C—Cl | NH | C₆H₅ (phenyl) | m.p.: 150° C. |
| 13 | Ib | 2 | 1 | Cl | H | CF₃ | H | C—Cl | NH | C₂H₅ | m.p.: 161° C. |
| 14 | Ia | 2 | 1 | Cl | H | CF₃ | H | C—Cl | NH | C₂H₅ | m.p.: 135° C. |
| 15 | Ib | 2 | 1 | Cl | H | CF₃ | H | C—Cl | NH | H | m.p.: 208° C. |
| 16 | Ia | 2 | 0 | Cl | H | CF₃ | H | C—Cl | — | pyrazol-1-yl | m.p.: 171° C. |
| 17 | Ia | 2 | 0 | Cl | H | CF₃ | H | C—Cl | — | imidazol-1-yl | m.p.: 172° C. |
| 18 | Ia | 2 | 0 | Cl | H | CF₃ | H | C—Cl | — | 3-methylpyrazol-1-yl | m.p.: 168° C. |
| 19 | Ia | 2 | 1 | Cl | H | CF₃ | H | C—Cl | O | H | m.p.: 280° C. |
| 20 | Ib | 0 | 0 | Cl | H | CF₃ | H | C—Cl | — | CH₃ | m.p.: 120° C. |
| 21 | Ia | 0 | 0 | Cl | H | CF₃ | H | C—Cl | — | CH₃ | m.p.: 123° C. |
| 22 | Ib | 2 | 1 | Cl | H | CF₃ | H | C—Cl | O | H | m.p.: 148° C. |
| 23 | Ia | 0 | 0 | Cl | H | CF₃ | H | C—Cl | — | —CH(CH₃)COOC₂H₅ | ¹H-NMR* 3,9 ppm —C$\underline{H}$—COOC₂H₅ / CH₃ |
| 24 | Ib | 0 | 0 | Cl | H | CF₃ | H | C—Cl | — | —CH(CH₃)COOCH₃ | ¹H-NMR* 3,9 ppm —C$\underline{H}$—COOCH₃ / CH₃ |
| 25 | Ib | 2 | 1 | Cl | H | CF₃ | H | C—F | O | Na | m.p.: 207° C. |
| 26 | Ib | 0 | 0 | Cl | H | CF₃ | H | C—Cl | — | —CH₂CH₂COOC₂H₅ | ¹H-NMR* |

TABLE 7-continued

Examples of the compounds of the formula (I)

| Example No. | Isomer group | m | n | $R^1$ | $R^2$ | $R^3$ | $R^4$ | X | Y | Z | Physical data |
|---|---|---|---|---|---|---|---|---|---|---|---|
| 27 | Ib | 2 | 0 | Cl | H | $CF_3$ | H | C—F | — | Cl | 3,2; 2,6 ppm —C$\underline{H}_2$—C$\underline{H}_2$— m.p.: 165° C. |
| 28 | Ib | 2 | 1 | Cl | H | $CF_3$ | H | C—F | NH | H | m.p.: 188° C. |
| 29 | Ib | 0 | 0 | Cl | H | $CF_3$ | H | C—Cl | — | (R)—*C̊HCOOCH$_3$ <br> \| <br> CH$_3$ | $^1$H-NMR* 3,9 ppm —C$\underline{H}$—COOCH$_3$ \| CH$_3$ |
| 30 | Ib | 0 | 0 | Cl | H | $CF_3$ | H | C—F | — | H | Fp: 89° C. |
| 31 | Ib | 0 | 0 | Cl | H | $CF_3$ | H | C—F | — | —CH—COOCH$_3$ <br> \| <br> CH$_3$ | $^1$H-NMR* 3,9 ppm —C$\underline{H}$—COOCH$_3$ \| CH$_3$ |
| 32 | Ib | 0 | 0 | Cl | H | $CF_3$ | H | C—F | — | —CH$_2$CH$_2$COOC$_2$H$_5$ | $^1$H-NMR* 3,2: 2,6 ppm —C$\underline{H}_2$—C$\underline{H}_2$— |
| 33 | Ib | 0 | 0 | Cl | H | $CF_3$ | H | C—F | — | (R)—*C̊HCOOCH$_3$ <br> \| <br> CH$_3$ | m.p.: 55° C. |
| 34 | Ib | 2 | 0 | Cl | H | $CF_3$ | H | C—Cl | — |  | m.p.: 209° C. |
| 35 | Ia | 2 | 1 | Cl | H | $CF_3$ | H | C—Cl | —NHCO— | C$_2$H$_5$ | m.p.: 162° C. |
| 36 | Ia | 2 | 1 | Cl | H | $CF_3$ | H | C—Cl | —NHCO— | C$_4$H$_9$ | m.p.: 163° C. |
| 37 | Ia | 2 | 1 | Cl | H | $CF_3$ | H | C—Cl | —NHCO— | CH$_3$ | m.p.: 206° C. |
| 38 | Id | 2 | 1 | Cl | H | $CF_3$ | H | C—Cl | O | Na | m.p.: >260° C. |
| 39 | Ie | 2 | 1 | Cl | H | $CF_3$ | H | C—Cl | O | Na | m.p.: >260° C. |
| 40 | Id | 2 | 0 | Cl | H | $CF_3$ | H | C—Cl | — | Cl | m.p.: 145° C. |
| 41 | Ie | 2 | 0 | Cl | H | $CF_3$ | H | C—Cl | — | Cl | m.p.: 135° C. |
| 42 | Id | 2 | 1 | Cl | H | $CF_3$ | H | C—Cl | O | H | m.p.: 105° C. |
| 43 | Ie | 2 | 1 | Cl | H | $CF_3$ | H | C—Cl | O | H | m.p.: 110° C. |
| 44 | Ie | 0 | 0 | Cl | H | $CF_3$ | H | C—Cl | — | H | m.p.: 185° C. |
| 45 | Ib | 2 | 1 | Cl | H | $CF_3$ | H | C—Cl | NH | —CH—COOC$_2$H$_5$ <br> \| <br> CH$_3$ | m.p.: 128° C. |
| 46 | Ib | 2 | 1 | Cl | H | $CF_3$ | H | C—F | NH | —CH—COOC$_2$H$_5$ <br> \| <br> CH$_3$ | m.p.: 97° C. |
| 47 | Ie | 0 | 0 | Cl | H | $CF_3$ | H | C—Cl | — | —CH—COOC$_2$H$_5$ <br> \| <br> CH$_3$ | m.p.: 98° C. |
| 48 | Ie | 0 | 0 | Cl | H | $CF_3$ | H | C—Cl | — | —CH—COOCH$_3$ <br> \| <br> CH$_3$ | (amorphous) |
| 49 | Ic | 0 | 0 | Cl | H | $CF_3$ | H | C—Cl | — | H | m.p.: 201° C. |
| 50 | Id | 2 | 1 | Cl | H | $CF_3$ | H | C—Cl | NH | H | m.p.: 185° C. |
| 51 | Ic | 0 | 0 | Cl | H | $CF_3$ | H | C—Cl | — | —CH—COOC$_2$H$_5$ <br> \| <br> CH$_3$ | (amorphous) |
| 52 | Ic | 0 | 0 | Cl | H | $CF_3$ | H | C—Cl | — | —CH—COOCH$_3$ <br> \| <br> CH$_3$ | m.p.: 68° C. |
| 53 | Ic | 2 | 1 | Cl | H | $CF_3$ | H | C—Cl | O | H | (amorphous) |
| 54 | Ie | 2 | 1 | Cl | H | $CF_3$ | H | C—Cl | —NHCOO— | —C$_2$H$_5$ | m.p.: 133° C. |
| 55 | Id | 2 | 1 | Cl | H | $CF_3$ | H | C—F | O | Na | m.p.: >260° C. |
| 56 | Id | 2 | 1 | Cl | H | $CF_3$ | H | C—Cl | O | Na | m.p.: >260° C. |

TABLE 7-continued

Examples of the compounds of the formula (I)

| Example No. | Isomer group | m | n | R¹ | R² | R³ | R⁴ | X | Y | Z | Physical data |
|---|---|---|---|---|---|---|---|---|---|---|---|
| 57 | Ic | 2 | 1 | Cl | H | CF₃ | H | C—Cl | NH | H | m.p.: 171° C. |
| 58 | Ie | 2 | 0 | Cl | H | CF₃ | H | C—Cl | — | ![3,5-dimethylpyrazol-1-yl] | m.p.: 158° C. |
| 59 | Ic | 2 | 0 | Cl | H | CF₃ | H | C—Cl | — | ![3,5-dimethylpyrazol-1-yl] | m.p.: 113° C. |
| 60 | Id | 2 | 0 | Cl | H | CF₃ | H | C—Cl | — | ![3,5-dimethylpyrazol-1-yl] | m.p.: 167° C. |
| 61 | Ie | 2 | 0 | Cl | H | CF₃ | H | C—Cl | — | ![pyrazol-1-yl] | m.p.: 84° C. |
| 62 | Ic | 2 | 0 | Cl | H | CF₃ | H | C—Cl | — | ![pyrazol-1-yl] | mp.: 163° C. |
| 63 | Id | 2 | 0 | Cl | H | CF₃ | H | C—F | — | Cl | m.p.: 117° C. |
| 64 | Ie | 2 | 0 | Cl | H | CF₃ | H | C—F | — | Cl | m.p.: 89° C. |
| 65 | Ib | 0 | 0 | Cl | H | CF₃ | H | C—Cl | — | —C(CH₃)₂COOC₂H₅ | |
| 66 | Ib | 0 | 0 | Cl | H | CF₃ | H | C—Cl | — | —CH(C₂H₅)COOC₂H₅ | |
| 67 | Ib | 0 | 0 | Cl | H | CF₃ | H | C—Cl | — | —CH(CH₃)OOCH(CH₃)COOC₂H₅ | |
| 68 | Ib | 0 | 0 | Cl | H | Cl | H | N | — | —CH(CH₃)COOCH₃ | |
| 69 | Ib | 0 | 0 | CN | H | CF₃ | H | CH | — | —CH(CH₃)COOCH₃ | |
| 70 | Ib | 0 | 0 | CN | H | CF₃ | H | CH | — | H | |
| 71 | Ib | 2 | 0 | CN | H | CF₃ | H | CH | — | Cl | m.p. 163° C. |
| 72 | Ib | 0 | 0 | Cl | H | Cl | H | N | — | H | |
| 73 | Ib | 2 | 0 | Cl | H | Cl | H | N | — | Cl | m.p. 140° C. |
| 74 | Ib | 0 | 0 | Cl | H | CF₃ | Cl | C—Cl | — | —CH(CH₃)—COOCH₃ | |
| 75 | Ib | 0 | 0 | Cl | H | CF₃ | Cl | C—Cl | — | H | |

TABLE 7-continued

Examples of the compounds of the formula (I)

| Example No. | Isomer group | m | n | $R^1$ | $R^2$ | $R^3$ | $R^4$ | X | Y | Z | Physical data |
|---|---|---|---|---|---|---|---|---|---|---|---|
| 76 | Ib | 2 | 0 | Cl | H | $CF_3$ | Cl | C—Cl | — | Cl | |
| 77 | Ib | 2 | 0 | Cl | H | $CF_3$ | F | C—Cl | — | Cl | |
| 78 | Ib | 0 | 0 | Cl | H | $CF_3$ | F | C—Cl | — | H | |
| 79 | Ib | 0 | 0 | Cl | H | $CF_3$ | H | C—Cl | — | —$CH_2COOCH_3$ | m.p. 77° C. |
| 80 | Ib | 2 | 1 | Cl | H | $CF_3$ | H | C—F | —NHCO— | $CH_3$ | m.p. 102° C. |
| 81 | Ib | 2 | 1 | Cl | H | $CF_3$ | H | C—Cl | —$NHSO_2$— | 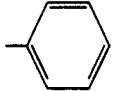 | m.p. 275° C. |
| 82 | Ib | 2 | 0 | Cl | H | $CF_3$ | H | CH | — | Cl | |
| 83 | Ic | 2 | 1 | Cl | H | $CF_3$ | H | C—Cl | O | Na | (amorphous) |
| 84 | Ic | 2 | 0 | Cl | H | $CF_3$ | H | C—Cl | — | Cl | m.p. 118° C. |
| 85 | Ie | 2 | 1 | Cl | H | $CF_3$ | H | C—Cl | NH | H | m.p. 210° C. |
| 86 | Ib | 2 | 1 | Cl | H | $CF_3$ | H | C—Cl | NH | —$CH_2COOC_2H_5$ | m.p. 131° C. |
| 87 | Ib | 2 | 1 | Cl | H | $CF_3$ | H | C—F | NH | —$CH_2COOC_2H_5$ | m.p. 88° C. |
| 88 | Id | 0 | 0 | Cl | H | $CF_3$ | H | C—Cl | — | H | (amorphous) |
| 89 | Id | 0 | 0 | Cl | H | $CF_3$ | H | C—Cl | — | —CH($CH_3$)$COOC_2H_5$ | (amorphous) |
| 90 | Id | 0 | 0 | Cl | H | $CF_3$ | H | C—Cl | — | —CH($CH_3$)$COOCH_3$ | (amorphous) |
| 91 | Ie | 2 | 1 | Cl | H | $CF_3$ | H | C—Cl | —NHCO— | $CH_3$ | m.p.: 142° C. |
| 92 | Id | 2 | 0 | Cl | H | $CF_3$ | H | C—F | — |  | m.p.: 151° C. |
| 93 | Ie | 2 | 0 | Cl | H | $CF_3$ | H | C—F | — |  | (amorphous) |
| 94 | Ib | 0 | 0 | Cl | H | $CF_3$ | H | C—F | — | —$CH_2COOCH_3$ | $^1$H-NMR* 3,7 ppm —$\underline{CH_2}$— |
| 95 | Ia | 2 | 1 | Cl | H | $CF_3$ | H | Cl | —NHCO— | —$C_2H_5$ | m.p.: 270° C. |
| 96 | Ic | 2 | 1 | Cl | H | $CF_3$ | H | C—Cl | —NHCOO— | —$C_2H_5$ | m.p.: 67° C. |
| 97 | Ie | 2 | 1 | Cl | H | $CF_3$ | H | C—F | —NH— | —$(CH_3)_2OCH_3$ | m.p.: 103° C. |
| 98 | Id | 0 | 0 | F | H | $CF_3$ | H | C—Cl | — | H | |
| 99 | Ie | 0 | 0 | F | H | $CF_3$ | H | C—Cl | — | H | m.p.: 74° C. |
| 100 | Ib | 0 | 0 | Cl | H | $CF_3$ | H | C—F | — | —$CH_2COOC_2H_5$ | |
| 101 | Ie | 0 | 0 | F | H | $CF_3$ | H | C—Cl | — | —CH($CH_3$)$COOC_2H_5$ | |
| 102 | Ie | 0 | 0 | F | H | $CF_3$ | H | C—Cl | — | —CH($CH_3$)—$COOC_2H_5$ | |
| 103 | Id | 0 | 0 | F | H | $CF_3$ | H | C—Cl | — | —CH($CH_3$)—$COOCH_3$ | |
| 104 | Id | 0 | 0 | Cl | H | $CF_3$ | H | C—F | — | —CH($CH_3$)—$COOC_2H_5$ | |
| 105 | Id | 0 | 0 | Cl | H | $CF_3$ | H | C—F | — | —$CH_2COOC_2H_5$ | |
| 106 | Ib | 2 | 1 | Cl | H | $CF_3$ | H | C—F | O | H | Oil |
| 107 | Ib | 0 | 0 | Cl | H | $CF_3$ | H | C—Cl | — | —C($CH_3$)$(COOC_2H_5)_2$ | Oil |
| 108 | Id | 2 | 0 | Cl | H | Cl | H | N | — | Cl | m.p.: 107° C. |

TABLE 7-continued

Examples of the compounds of the formula (I)

| Example No. | Isomer group | m | n | R¹ | R² | R³ | R⁴ | X | Y | Z | Physical data |
|---|---|---|---|---|---|---|---|---|---|---|---|
| 109 | Id | 2 | 1 | Cl | H | Cl | H | N | O | Na | m.p. >260° C. |
| 110 | Ic | 0 | 0 | F | H | CF₃ | H | C—Cl | — | —CH(CH₃)—COOC₂H₅ | Oil |
| 111 | Ic | 0 | 0 | F | H | CF₃ | H | C—Cl | — | —CH(CH₃)—COOCH₃ | Oil |
| 112 | Ic | 0 | 0 | F | H | CF₃ | H | C—Cl | — | —CH₂—COOC₂H₅ | Oil |
| 113 | Id | 2 | 1 | Cl | H | CF₃ | H | C—Cl | —N(H)—COO— | —C₂H₅ | m.p. 155° C. |
| 114 | Ie | 2 | 1 | Cl | H | CF₃ | H | C—Cl | —N(H)— | —CH₂COOC₂H₅ | m.p. 115° C. |
| 115 | Ib | 2 | 1 | Cl | H | CF₃ | H | N | O | Na | m.p. >300° C. |
| 116 | Ib | 2 | 0 | Cl | H | CF₃ | H | N | — | Cl | m.p. 147° C. |
| 117 | Ib | 2 | 0 | Cl | H | CF₃ | H | C—Cl | — | —CH(CH₃)COOCH₃ | m.p. 122° C. |
| 118 | Ib | 2 | 1 | CN | H | CF₃ | H | CH | O | Na | m.p. >300° C. |
| 119 | Ib | 2 | 1 | Cl | H | CF₃ | H | N | NH | H | m.p. 192° C. |
| 120 | Ib | 0 | 0 | Cl | H | CF₃ | H | N | — | —CH(CH₃)COOCH₃ | (amorphous) |
| 121 | Ib | 2 | 1 | CN | H | CF₃ | H | CH | NH | H | m.p. 158° C. |
| 122 | Id | 0 | 0 | CN | H | CF₃ | H | CH | — | H | m.p. 100° C. |
| 123 | Ib | 2 | 1 | Cl | H | CF₃ | H | N | —NHCO— | —CH₃ | m.p. 172° C. |
| 124 | Ib | 2 | 1 | CN | H | CF₃ | H | CH | —NHCO— | —CH₃ | m.p. 205° C. |
| 125 | Ib | 0 | 0 | CN | H | CF₃ | H | CH | — | —CH₂COOCH₃ | (amorphous) |
| 126 | Ib | 0 | 0 | Cl | H | CF₃ | H | C—F | — | —C(CH₃)₂COOC₂H₅ | (amorphous) |
| 127 | Ia | 0 | 0 | Cl | H | CF₃ | H | C—Cl | — | —CH₂COOCH₃ | m.p. 114° C. |
| 128 | Ib | 0 | 0 | Cl | H | CF₃ | H | C—Cl | — | —CH(CH₃)COOH | m.p. 148° C. |
| 129 | Ib | 2 | 1 | Cl | H | Cl | H | N | O | Na | m.p. >260° C. |
| 130 | Ib | 0 | 0 | Cl | H | Cl | H | N | — | —CH₂COOCH₃ | m.p. 115° C. |
| 131 | Id | 2 | 1 | Cl | H | CF₃ | H | C—Cl | NH | —CH(CH₃)COOC₂H₅ | m.p. 103° C. |
| 132 | Ie | 2 | 1 | Cl | H | CF₃ | H | C—F | O | Na | m.p. >260° C. |
| 133 | Ic | 2 | 0 | Cl | H | CF₃ | H | C—F | — | 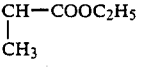 | m.p. 78° C. |
| 134 | Id | 2 | 1 | Cl | H | Cl | H | N | NH | H | m.p. 103° C. |
| 135 | Id | 2 | 1 | Cl | H | CF₃ | H | N | O | Na | m.p. >250° C. |
| 136 | Id | 2 | 0 | Cl | H | CF₃ | H | N | — | Cl | m.p. 138° C. |
| 137 | Id | 2 | 1 | Cl | H | CF₃ | H | N | NH | H | m.p. 140° C. |
| 138 | Id | 2 | 1 | Cl | H | CF₃ | H | N | —NH—COO— | C₂H₅ | m.p. 88° C. |
| 139 | Id | 0 | 0 | Cl | H | CF₃ | H | C—F | — | —(CH₂)₃COOC₂H₅ | (amorphous) |
| 140 | Id | 0 | 0 | Cl | H | CF₃ | H | C—F | — | —(CH₂)₂COOC₂H₅ | (amorphous) |
| 141 | Ic | 0 | 0 | Cl | H | CF₃ | H | C—Cl | — | —CH₂COOCH₃ | (amorphous) |

TABLE 7-continued

Examples of the compounds of the formula (I)

| Example No. | Isomer group | m | n | $R^1$ | $R^2$ | $R^3$ | $R^4$ | X | Y | Z | Physical data |
|---|---|---|---|---|---|---|---|---|---|---|---|
| 142 | Ic | 0 | 0 | Cl | H | $CF_3$ | H | C—F | — | —$CH_2COOCH_3$ | (amorphous) |

*The $^1$H-NMR spectra were recorded in $DCCl_3$ using tetramethylsilane as the internal standard. The chemical shifts are stated as δ values for the groupings. C$\underline{H}_2$—.bzw. —C$\underline{H}_2$C$\underline{H}_2$— bzw. —C$\underline{H}$—CH$_3$.

USE EXAMPLES

The compound shown below is used as the comparison substance in the use example which follows:

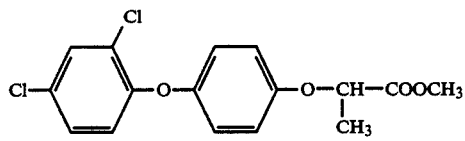

methyl α-[4-(2,4-dichloro-phenoxy)-phenoxy]-propionate (diclofop-methyl) (known from DE-OS (German Published Specification) No. 2,223,894/Example 86).

EXAMPLE A

Post-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5 - 15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, a clearly superior activity compared with the prior art is shown, for example, by the compounds according to Preparation Examples: (9), (23) (24), (94) and (142).

What is claimed is:

1. An aryloxynaphthalene or heteroaryloxynaphthalene having a substituent bonded via sulphur and of the formula

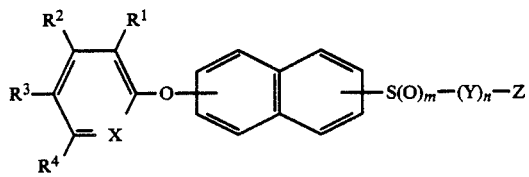

in which
m represents the numbers 0, 1 or 2,
n represents the numbers 0 or 1,
$R^1$ represents hydrogen, halogen, cyano or trifluoromethyl,
$R^2$ represents hydrogen or halogen,
$R^3$ represents halogen, trifluoromethyl, trifluoromethoxy, trifluoromethylthio or trifluoromethylsulphonyl,
$R^4$ represents hydrogen or halogen,
X represents nitrogen or the grouping C—$R^5$, wherein
$R^5$ represents hydrogen or halogen,
Y represents oxygen or one of the groupings

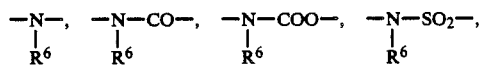

wherein $R^6$ represents hydrogen, $C_1$-$C_4$-alkyl, —CO—Z or —$SO_2$—Z and
Z represents hydrogen or halogen, or $C_1$-$C_6$-alkyl which is optionally substituted by halogen, cyano, carboxyl, $C_1$-$C_4$-alkoxy, $C_1$-$C_4$-alkylcarbonyl, $C_1$-$C_4$-alkoxy-carbonyl, $C_1$-$C_4$-alkoxy-carbonyl-$C_1$-$C_4$-alkoxycarbonyl and/or $C_1$-$C_4$-alkylaminocarbonyl; or $C_3$-$C_6$-cycloalkyl or $C_3$-$C_6$-cycloalkyl-$C_1$-$C_4$-alkyl, in each case optionally substituted by halogen and/or $C_1$-$C_4$-alkyl; or $C_2$-$C_6$-alkenyl or $C_2$-$C_6$-alkinyl, in each case optionally substituted by halogen, cyano, carboxyl and/or $C_1$-$C_4$-alkoxy-carbonyl; or phenyl, naphthyl, phenyl-$C_1$-$C_4$-alkyl or naphthyl-$C_1$-$C_4$-alkyl, in each case optionally substituted by halogen, cyano, carboxyl, nitro, $C_1$-$C_4$-alkyl, $C_1$-$C_2$-halogenoalkyl, $C_1$-$C_4$-alkoxy, $C_1$-$C_4$-alkoxy, $C_1$-$C_2$-halogenoalkoxy, $C_1$-$C_4$-alkylthio, $C_1$-$C_2$-halogenoalkylthio, $C_1$-$C_4$-alkylsulphinyl, $C_1$-$C_4$-alkylsulphonyl, di-($C_1$-$C_2$-alkyl)-aminosulphonyl, di-($C_1$-$C_2$-alkyl)aminocarbonyl, di-($C_1$-$C_2$-alkyl)-amino, $C_1$-$C_4$-alkoxycarbonyl and/or $C_1$-$C_2$-alkylenedioxy; or Z represents pyrazolyl, imidazolyl and triazolyl, which is optionally substituted by halogen, $C_1$-$C_4$-alkyl, $C_1$-$C_2$-halogenoalkyl, $C_1$-$C_4$-alkoxy and/or $C_1$-$C_2$-halogenoalkoxy,
or a salt thereof.

2. A compound according to claim 1, in which
m represents the numbers 0, 1 or 2,
n represents the numbers 0 or 1,
$R^1$ represents hydrogen, fluorine, chlorine, bromine, cyano or trifluoromethyl,
$R^2$ represents hydrogen, fluorine or chlorine,
$R^3$ represents fluorine, chlorine, bromine, trifluoromethyl, trifluoromethoxy, trifluoromethylthio or trifluoromethylsulphonyl,
$R^4$ represents hydrogen, fluorine or chlorine,
X represents nitrogen or the grouping C—$R^5$, and
R5 represents hydrogen, fluorine, chlorine or bromine.

3. A compound according to claim 1, in which
$R^1$ represents cyano, fluorine or chlorine,
$R^2$ represents hydrogen, fluorine or chlorine,
$R^3$ represents chlorine, trifluoromethyl or trifluoromethylsulphonyl,
$R^4$ represents hydrogen, fluorine or chlorine,
X represents nitrogen or the grouping C—$R^5$, wherein
$R^5$ represents hydrogen, fluorine or chlorine, and
(A) m represents the number 0,
n represents the number 0, and
Z represents hydrogen, $C_1$–$C_4$-alkyl which is optionally substituted by fluorine, chlorine, cyano, carboxyl, $C_1$–$C_4$-alkoxy-carbonyl, $C_1$–$C_4$-alkoxy-carbonyl-$C_1$–$C_2$-alkoxy-carbonyl and/or $C_1$–$C_4$-alkylamino-carbonyl; or $C_3$–$C_4$-alkenyl which is optionally substituted by fluorine, chlorine, cyano, carboxyl and/or $C_1$–$C_4$-alkoxy-carbonyl; or benzyl which is optionally substituted by fluorine, chlorine and/or methyl, or
(B) m represents the number 2,
n represents the numbers 0 or 1,
Y represents oxygen or one of the groupings —NH—, —NH—CO—, —NH—COO— or —NH—$SO_2$, and
Z represents hydrogen, or $C_1$–$C_4$-alkyl which is optionally substituted by fluorine, chlorine, cyano, carboxyl, $C_1$–$C_4$-alkoxycarbonyl and/or $C_1$–$C_4$-alkylamino-carbonyl; or $C_3$–$C_4$-alkenyl which is optionally substituted by fluorine, chlorine, cyano, carboxyl and/or $C_1$–$C_4$-alkoxy-carbonyl; or phenyl or benzyl, in each case optionally substituted by fluorine, chlorine, bromine, nitro, methyl, ethyl, trifluoromethyl, methoxy, ethoxy, difluoromethoxy, trifluoromethoxy, chlorodifluoromethoxy, methylthio, difluoromethylthio, trifluoromethylthio, chlorodifluoromethylthio, methylsulphonyl, dimethylaminosulphonyl, methoxycarbonyl and/or ethoxy-carbonyl, or
(C) m represents the number 2,
n represents the number 0 and
Z represents chlorine, pyrazolyl which is optionally substituted by chlorine and/or $C_1$–$C_3$-alkyl, or imidazolyl which is optionally substituted by $C_1$–$C_3$-alkyl.

4. A herbicidal composition comprising at least one compound according to claim 1 and a suitable extender and/or carrier.

5. A method of combating weeds, comprising applying to said weeds and/or their environment an effective amount of at least one compound according to claim 1.

6. A compound according to claim 1 of the formula

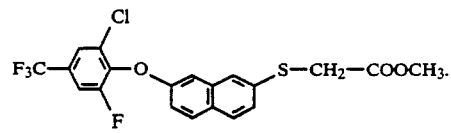

7. A compound according to claim 1 of the formula

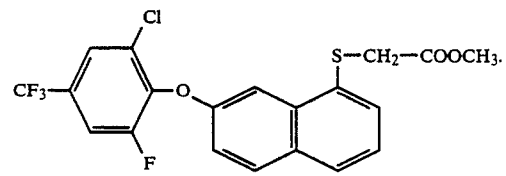

* * * * *

UNITED STATES PATENT AND TRADEMARK OFFICE
CERTIFICATE OF CORRECTION

PATENT NO. : 4,952,235

DATED : August 28, 1990

INVENTOR(S) : Andree et al.

It is certified that error appears in the above-identified patent and that said Letters Patent is hereby corrected as shown below:

Col. 42, line 45   Delete " $C_1$-$C_4$-alkoxy, " second occurrence

Signed and Sealed this

Seventh Day of July, 1992

Attest:

DOUGLAS B. COMER

Attesting Officer    Acting Commissioner of Patents and Trademarks